United States Patent
Tompkins

(10) Patent No.: US 9,486,334 B2
(45) Date of Patent: Nov. 8, 2016

(54) VACUUM PROSTHESIS WITH FORCE SENSING MEMBER

(75) Inventor: Michael E. Tompkins, Austin, TX (US)

(73) Assignee: Hanger, Inc., Austin, TX (US)

(*) Notice: Subject to any disclaimer, the term of this patent is extended or adjusted under 35 U.S.C. 154(b) by 208 days.

(21) Appl. No.: 13/306,424

(22) Filed: Nov. 29, 2011

(65) Prior Publication Data

US 2012/0143351 A1 Jun. 7, 2012

Related U.S. Application Data

(60) Provisional application No. 61/418,724, filed on Dec. 1, 2010.

(51) Int. Cl.
| | | |
|---|---|---|
| *A61F 2/80* | (2006.01) | |
| *A61B 5/103* | (2006.01) | |
| *A61B 5/11* | (2006.01) | |
| *A61B 5/00* | (2006.01) | |
| *A61F 2/68* | (2006.01) | |
| *A61F 2/70* | (2006.01) | |
| *A61F 2/74* | (2006.01) | |

(Continued)

(52) U.S. Cl.
CPC ............... *A61F 2/80* (2013.01); *A61B 5/1038* (2013.01); *A61B 5/1123* (2013.01); *A61B 5/4851* (2013.01); *A61B 5/6811* (2013.01); *A61B 5/6828* (2013.01); *A61F 2/68* (2013.01); *A61B 2560/0257* (2013.01); *A61B 2562/0247* (2013.01); *A61B 2562/046* (2013.01); *A61F 2002/689* (2013.01); *A61F 2002/704* (2013.01); *A61F 2002/705* (2013.01); *A61F 2002/707* (2013.01); *A61F 2002/742* (2013.01); *A61F 2002/764* (2013.01); *A61F 2002/7635* (2013.01); *A61F 2002/7655* (2013.01); *A61F 2002/7818* (2013.01); *A61F 2002/802* (2013.01)

(58) Field of Classification Search
CPC .......... A61F 2/72; A61F 2/7843; A61F 2/80; A61F 2002/5032; A61F 2002/742; A61F 2002/7635; A61F 2002/7655; A61F 2002/802; A61F 2002/805; A61F 2002/807; A61F 2/68; A61B 5/4851; A61B 5/6811
USPC .............................................. 623/33, 34, 36
See application file for complete search history.

(56) References Cited

U.S. PATENT DOCUMENTS 5,993,400 A * 11/1999 Rincoe et al. ................. 600/595
6,231,616 B1 * 5/2001 Helmy ............................ 623/34

(Continued)

OTHER PUBLICATIONS

Zhang, M. Clinical investigation of the pressure and shear stress on the trans-tibial stump with a prosthesis. Medical Engineering & Physics. Dec. 1997.*

*Primary Examiner* — Bruce E Snow
*Assistant Examiner* — Melissa Hoban
(74) *Attorney, Agent, or Firm* — Foley & Lardner LLP

(57) ABSTRACT

A prosthetic device includes a socket assembly defining a cavity and configured to receive a portion of a residual limb of a user within the cavity, a force sensing member configured to detect forces applied to the residual limb at a plurality of locations about the portion of the residual limb and generate signals based on the detected force, a vacuum system in fluid communication with the socket and configured to control an amount of vacuum applied to the cavity, and a controller coupled to the force sensing member and the vacuum system. The controller is configured to receive the signals from the force sensing member and control operation of the vacuum system during use of the prosthetic device by the user based at least in part on the signals received from the force sensing member.

10 Claims, 5 Drawing Sheets

(51) Int. Cl.
*A61F 2/76* (2006.01)
*A61F 2/78* (2006.01)

(56) References Cited

U.S. PATENT DOCUMENTS

| | | |
|---|---|---|
| 7,377,944 B2* | 5/2008 | Janusson et al. ............... 623/36 |
| 2004/0167638 A1* | 8/2004 | Caspers ........................ 623/27 |
| 2006/0212128 A1* | 9/2006 | Nachbar ........................ 623/24 |
| 2007/0055383 A1* | 3/2007 | King ............................... 623/34 |
| 2007/0191965 A1* | 8/2007 | Colvin et al. ................... 623/34 |
| 2008/0086218 A1* | 4/2008 | Egilsson ......................... 623/34 |
| 2010/0125342 A1* | 5/2010 | King ............................... 623/34 |
| 2011/0060421 A1* | 3/2011 | Martin et al. .................. 623/34 |
| 2011/0118853 A1* | 5/2011 | Kirn ............................... 623/34 |
| 2012/0191218 A1* | 7/2012 | McCarthy ...................... 623/34 |

* cited by examiner

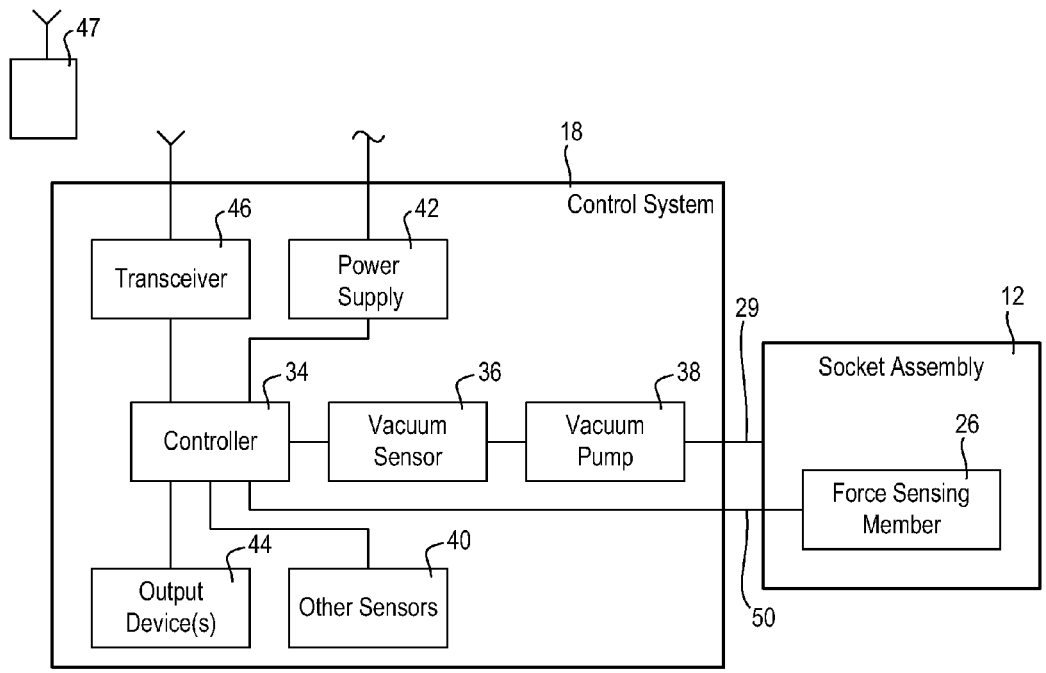
FIG. 3
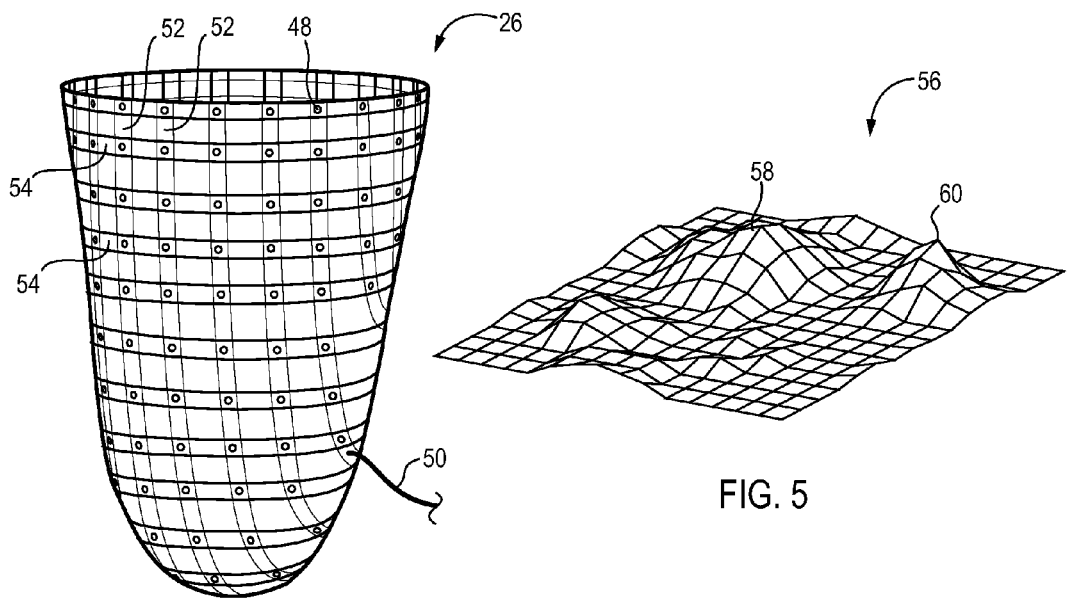
FIG. 4
FIG. 5

VACUUM PROSTHESIS WITH FORCE SENSING MEMBER

CROSS-REFERENCE TO RELATED PATENT APPLICATIONS

The present application claims the benefit of U.S. Provisional Application No. 61/418,724, filed Dec. 1, 2010, which is incorporated by reference herein in its entirety. The present application is related to International Patent Application No. PCT/US2009/046497, filed Jun. 5, 2009, published as International Publication No. WO2009/149412, which is incorporated by reference herein in its entirety.

BACKGROUND

The present disclosure relates generally to the field of prosthetic devices, and more specifically, to methods and systems related to vacuum prosthetic devices having force sensing features.

Prosthetic devices such as lower limb prosthetics often include a socket having an inner cavity that receives a portion of a residual limb of a user. A vacuum system may be used to create a vacuum within the space between the inner cavity of the socket and the residual limb.

There are many challenges associated with maintaining a proper vacuum level in a prosthetic device in order to, for example, ensure proper operation of the prosthetic device and provide a comfortable fit for users of such devices. As such, it would be desirable to provide an improved prosthetic device that addresses these challenges.

SUMMARY

One embodiment relates to a prosthetic device comprising a socket assembly defining a cavity and configured to receive a portion of a residual limb of a user within the cavity; a force sensing member configured to detect forces applied to the residual limb at a plurality of locations about the portion of the residual limb and generate signals based on the detected force; a vacuum system in fluid communication with the socket and configured to control an amount of vacuum applied to the cavity; and a controller coupled to the force sensing member and the vacuum system, the controller configured to receive the signals from the force sensing member and control operation of the vacuum system during use of the prosthetic device by the user based at least in part on the signals received from the force sensing member.

Another embodiment relates to a method comprising applying an amount of vacuum to a cavity defined by a socket and a portion of a residual limb of a user, the portion of the residual limb received within the socket; detecting forces experienced by the residual limb at a plurality of locations about the portion of the residual limb during use of the prosthetic device by the user; providing signals to a controller based on the forces detected at the plurality of locations; and controlling the amount of vacuum applied to the cavity based on the signals.

Another embodiment relates to a method comprising detecting forces experienced by a residual limb at a plurality of locations about a portion of the residual limb during use of a prosthetic device; providing signals to a controller based on the forces detected at the plurality of locations; and selectively controlling an amount of vacuum applied to each of a plurality of localized regions on the residual limb based on the signals.

BRIEF DESCRIPTION OF THE DRAWINGS

The present disclosure will become more fully understood from the following detailed description, taken in conjunction with the accompanying drawings, wherein like reference numerals refer to like elements.

FIG. 3 is a schematic block diagram of a control system of the prosthetic device of FIG. 1 according to an exemplary embodiment.

FIG. 4 is a perspective view of a force sensing member of the prosthetic device of FIG. 1 according to an exemplary embodiment.

FIG. 5 is a is a perspective view of a force distribution graph illustrating the force distribution about a force sensing member according to an exemplary embodiment.

DETAILED DESCRIPTION OF EXEMPLARY EMBODIMENTS

Referring generally to the FIGURES, various embodiments of prosthetic devices are shown according to exemplary embodiments. Though various embodiments herein are described in the context of an artificial leg, it is contemplated that the present disclosure is equally applicable to other contexts in which a device is connected to a user's body. For example, the device could be an artificial arm, an orthotic component, or other prosthetic/orthotic products that use vacuum or similar methods to connect to a user. The connection method need not be a fully encompassing socket like a prosthesis. Further, a vacuum could assist a connection device or may be used as a stabilizer in connection with various connection methods.

Figure 1:
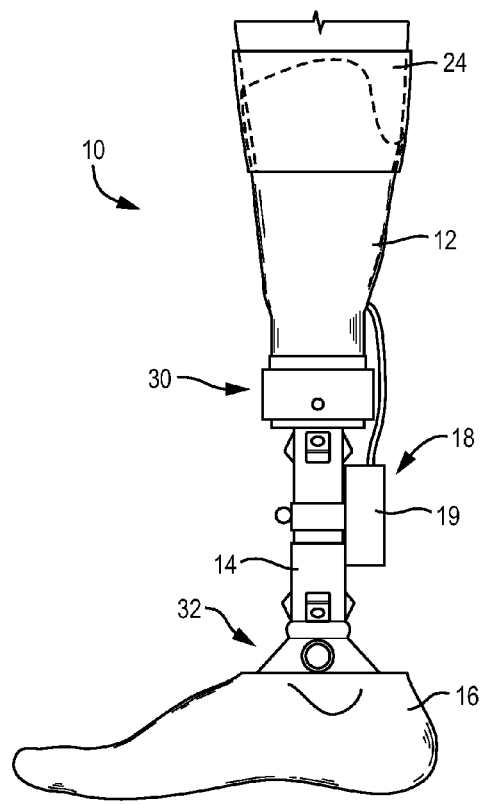
FIG. 1 is a perspective view of a prosthetic device fitted to residual limb of a user according to an exemplary embodiment.

Referring to FIG. 1, a prosthetic device 10 is shown according to an exemplary embodiment. Device 10 includes a socket assembly 12, a pylon 14, an artificial foot 16, and a control system 18. Device 10 is intended to restore functionality to patients having lost limbs such as legs, arms, and the like. Generally, socket assembly 12 receives a portion of a residual limb of a user. Pylon 14 is a mechanical structure that provides a mechanical support and interface between socket assembly 12 and artificial foot 16. Artificial foot 16 may be designed to replicate a real foot (or, similarly, a hand, etc., depending on the particular application). As described in greater detail below, control system 18 controls an amount of vacuum applied to the socket assembly 12, where the vacuum provides a negative pressure to maintain the residual limb securely in place within the socket assembly. Based on various factors, control system 18 may vary the vacuum applied to socket assembly 12 to optimize the performance of device 10 for users.

Figure 2:
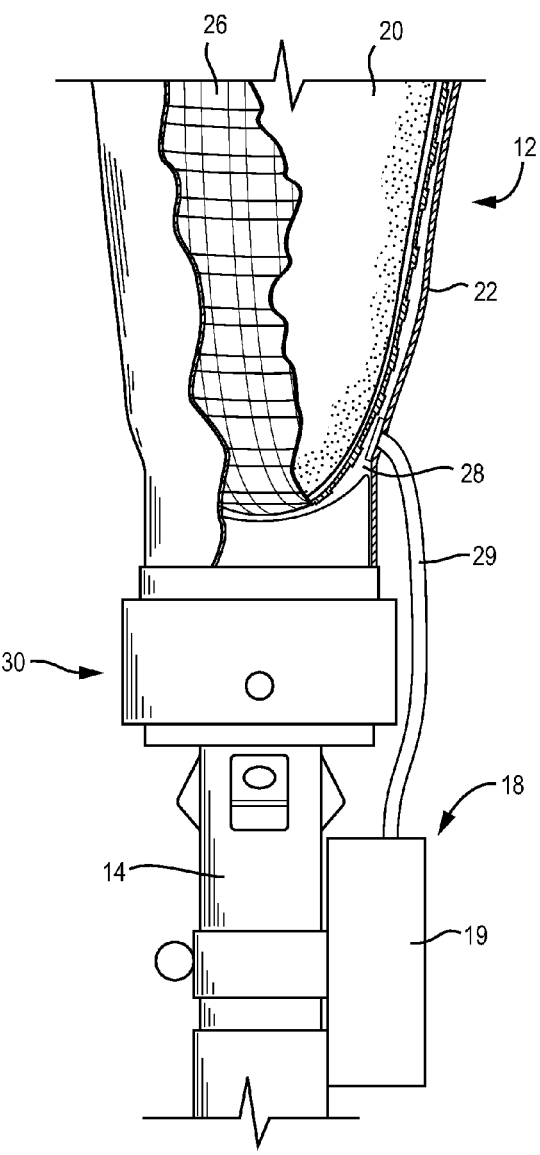
FIG. 2 is a partial cross-sectional view of the prosthetic device of claim 1 according to an exemplary embodiment.

Referring to FIGS. 1-2, according to one embodiment, a residual limb of a user is received within an inner liner 20. Inner liner 20 may be configured to fit around the residual limb and into outer casing 22. In some embodiments, inner liner may be formed of conventional liner material. The particular size and/or shape of inner liner 20 may vary depending on the user and the particular device 10 being utilized. According to one embodiment, inner liner 20 is configured to wick excessive moisture away from the surface of the residual limb to avoid discomfort to the user and/or improper fit of device 10.

According to an exemplary embodiment, an outer casing 22 may be provided with a size and shape customized to a particular user such that a substantial portion of a residual limb may be received within the interior of outer casing 22. As shown in FIG. 2, a cavity 28 may remain after insertion of the residual limb and inner liner 20 into outer casing 22 and prior to application of a vacuum to socket assembly 12. As discussed below, a desired vacuum can be applied to cavity 28 to provide a proper fit between the residual limb and outer casing 22.

According to an exemplary embodiment, sealing sleeve 24 may be configured to form an airtight seal between the residual limb and outer casing 22. For example, sealing sleeve 24 may in some embodiments be a non-foamed, nonporous polyurethane suspension sleeve that rolls over and covers a portion of outer casing 22 and a portion of the residual limb. The inner surface of sealing sleeve 24 may provide a seal against the skin on the user's thigh and the outer surface of the prosthetic socket to provide an airtight seal for the vacuum. Sealing sleeve 24 may be applied over the outer surface of outer casing 22 and rolled up onto the thigh portion of the residual limb after inner liner 20 is fit properly to the residual limb, and inner liner 20 and the residual limb are positioned within outer casing 22. Sealing sleeve 24 can provide a vacuum seal to enable device 10 to achieve appropriate vacuum (measured in, e.g., inches of mercury) and prosthetic suspension.

According to an exemplary embodiment, pylon 14 is attached to socket assembly 12 at an upper portion 30 of pylon 14. According to some embodiments, pylon 14 and socket assembly 12 may be coupled using a locking pin, such that a pin extending from a lower portion of socket assembly 12 is lockably received within a recess, or aperture, within pylon 14. Any other suitable means may be used to couple socket assembly 12 and pylon 14. Lower portion 32 of pylon 14 may be coupled to and/or form a part of artificial foot 16. Any suitable coupling means may be used to couple pylon 14 to artificial foot 16.

According to an exemplary embodiment, artificial foot 16 is configured to substantially replicate an actual human foot in shape, size, and/or range of motion. As indicated above, while the embodiments disclosed herein generally refer to a lower limb prosthetic device used in connection with an artificial foot, the teachings herein extend to other applications, including upper limb prosthetics and other devices that would benefit from the features disclosed herein. Artificial foot 16 may be made any suitable material, and the shape, size, and other characteristics of artificial foot 16 may be varied from those described herein to suit a particular user and/or application.

Figure 8:
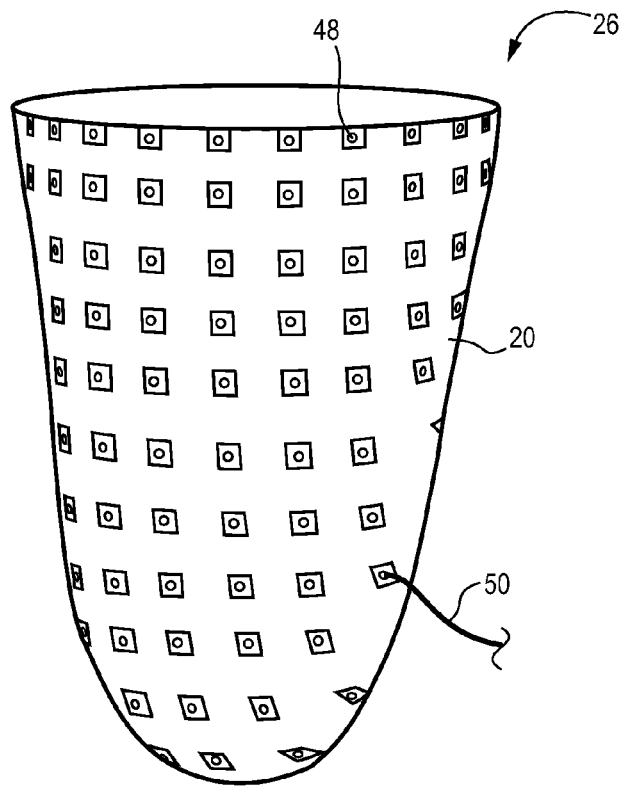
FIG. 8 is a perspective view of a force sensing member according to an exemplary embodiment.
Figure 9:
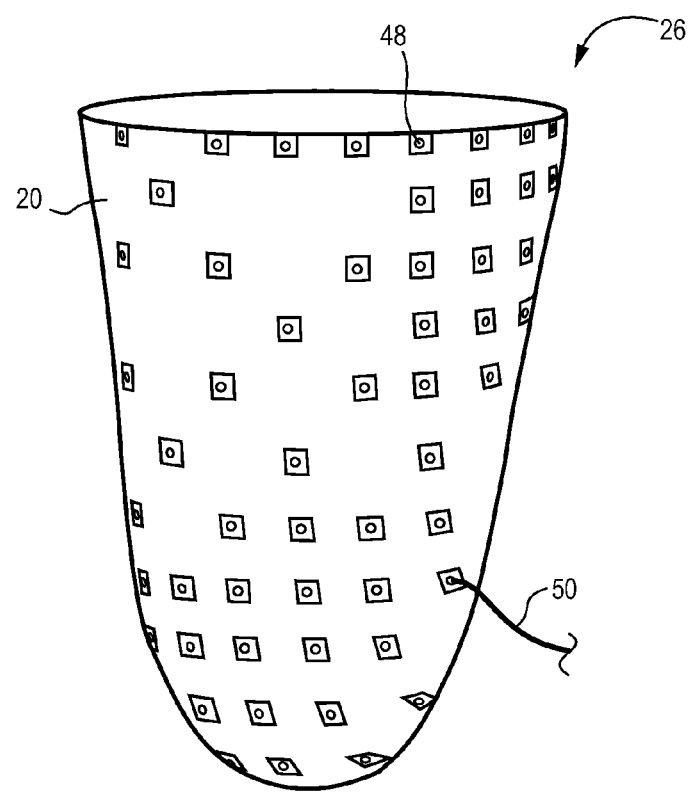
FIG. 9 is a perspective view of a force sensing member according to an exemplary embodiment.

Referring to FIGS. 2-5 and 8-11, according to an exemplary embodiment, a force sensing member 26 provides a plurality of force sensors 48 that are distributed over the surface of or within force sensing member 26. Force sensing member 26 detects forces acting upon the residual limb and transmits signals (e.g., via a wired connection 50 and/or a wireless connection via transceiver 46) to controller 34 based on the forces detected. While the embodiments herein generally refer to forces and force sensors, the embodiments are equally applicable to pressure sensors (e.g., sensors that determine forces applied over a certain area). Force sensors 48 are configured to sense the force experienced by the residual portion of the limb through inner liner 20. In some embodiments, as shown in FIG. 8, force sensors 48 may be distributed generally evenly by providing a matrix of generally evenly spaced force sensors 48. Alternatively, as shown in FIG. 9, a plurality of force sensors 48 may be provided that are distributed unevenly at desired places (e.g., locations known to experience significant forces, changes in forces, etc., due to changes in user activity, changes in user position (e.g., standing versus sitting etc.), changes in a user's pace of walking, jogging, etc., and the like). For example, in areas that experience fewer changes in the force applied to the residual limb (e.g., at the lateral sides of the residual limb), fewer force sensors may be used, whereas in areas where forces on the residual limb may be greater or subject to larger fluctuations (e.g., on the anterior/posterior walls and the distal end of the residual limb), more force sensors may be utilized. The placement, number, density, etc., of force sensors 48 used in connection with force sensing member 26 may be varied to suit a particular application, a particular user (e.g., height, weight, etc.), a type, shape, size, etc. of residual limb, and so on.

In some embodiments, force sensors 48 may be integrated into liner 20 or provided as part of a separate component from liner 20. For example, each sensor 48 may have a wired connection extending from the force sensor. Control electronics may be coupled to the liner (or another component of the socket assembly) to compile the data from the various force sensors and then transmit formatted signals to control system 18 via wired connection 50. As such, rather than sending a number of different wires/conductors to control system 18, the number of individual conductors may be minimized. According to an alternative embodiment, the communications between the control electronics coupled to the socket assembly and control system 18 may be wireless. According to another embodiment, a conductive pin lock may be used (e.g., similar to a phono jack) where control signals are provided over the power transmission.

According to an exemplary embodiment, force sensing member 26 may include a plurality of overlapping strips of material 52, 54, that may be arranged such that force sensors 48 are defined by the intersections of strips 52 and strips 54. For example, referring to FIG. 4, force sensors 48 are defined by the intersections of strips 52, 54. According to one embodiment, force sensing member 26 may include overlapping strips of flexible polymer material (e.g., utilizing the ZEBRA System available from Sensortech Corporation, of Greenville, S.C.). According to various other embodiments, the individual force sensors may be provided utilizing different materials and or components in connection with force sensing member 26 (e.g., Tekscan Flexiforce sensors available from Tekscan, Inc., of South Boston, Mass.). Referring to FIG. 5, force sensing member 26 may enable users to generate graphical views of the force distribution over the surface of the residual limb (e.g., viewable on remote terminal 47 or another device). For example, FIG. 5 shows an exemplary embodiment of a graphical depiction 56 showing points 58, 60 of increased force/pressure detected upon the residual limb. As discussed in greater detail below, the vacuum within socket assembly 12 may in turn be controlled based on these detected forces.

Referring now to FIG. 3, control system 18 is shown in greater detail according to an exemplary embodiment. As shown in FIG. 3, control system 18 includes a controller 34, a vacuum sensor 36, a vacuum pump 38, other sensors 40, a power supply 42, a transceiver 46, and output device(s) 44. According to various alternative embodiments, control system 18 may include more or fewer components than those described herein. Furthermore, while various components are shown as being independent from one another, in various alternative embodiments, one or more of the components of control system 18 may be combined, and similarly, individually shown components may be divided further into sub-components.

Referring further to FIG. 3, controller 34 may include a microprocessor, memory, and other electronics components required to control the operation of the other various components of control system 18 and device 10. As discussed in greater detail below, controller 34 may be configured to control the operation of various components of device 10 (e.g., vacuum pump 38, output device(s) 44, etc.) based on input signals received from other components of device 10 (e.g., force sensing member 26, vacuum sensor 36, etc.).

Vacuum Sensor 36 may be configured to detect the pressure, or vacuum level, within socket assembly 12 (e.g., within cavity 28) and to generate signals representing the detected pressure. The signals generated by sensor 36 are provided to controller 34 for further processing. Any suitable sensor may be utilized, and sensor 36 may be positioned within housing 19, adjacent socket assembly 12, or at any other suitable or desirable position.

Vacuum pump 38 is connected to socket assembly 12 via a fluid connection 29 that provides fluid communication between pump 38 and cavity 28 of socket assembly 12. Any suitable pump may be utilized (e.g., a diaphragm pump driven by a DC motor, etc.). Operation of pump 38 creates the partial vacuum in cavity 28 that in turn secures the residual limb to socket assembly 12. As discussed in greater detail below, controller 34 may control the operation of pump 38, and therefore the vacuum within cavity 28, based on a number of different factors, or inputs, either alone or in combination with each other. Vacuum pump 38 may be located within housing 19, or at other locations on device 10. For example, according to one embodiment, pump 38 may be provided adjacent the lower portion of socket assembly 12 and "in-line" with pylon 14 (e.g., such that the vacuum pump forms part of the structural support for socket assembly 12). Alternatively, pump 38 may be coupled to an exterior portion or surface of socket assembly 12.

Other sensors 40 may further be provided as part of control system 18 according to various other embodiments. For example, sensors 40 may include a barometric sensor that senses the current barometric pressure and provides corresponding signals to controller 34. Based on these signals, controller 34 may calibrate the other sensors (e.g., vacuum sensor 36) based on the current atmospheric pressure such that device 10 may accommodate changes in altitude, etc. Sensors 40 may further include an acceleration or orientation sensor that provides signals to controller 34 based on the acceleration and/or orientation of device 10. The acceleration or orientation sensor may be configured to detect a wide range of parameters, including acceleration, inclination, pitch, yawl, roll, dynamic movement data, static angular data, and so on. According to various other embodiments, additional and/or different sensors may be utilized in connection with device 10, and controller may take into account various data received from the sensors individually or in combination. Furthermore, based on the type of sensor and the particular prosthetic device, the position of the sensors may be varied to ensure that the proper parameters may be accurately detected.

Power supply 42 may be configured to supply the necessary power to the components of control system 18 and/or other components of device 10 (e.g., additional sensors, pumps, user interface devices, etc.). According to one embodiment, power supply 42 comprises a battery. According to various alternative embodiments, the battery may be a rechargeable, replaceable, and/or removeable battery. Any suitable battery may be used, including a lithium-ion battery, a lithium polymer batter, etc. For example, in one embodiment, the battery is a 3.7 Volt lithium ion battery. In some embodiments, power supply 42 may further include an interface (e.g., an electrical plug/socket) configured to received power from an external power supply (e.g., to recharge one or more batteries, to provide power during clinical evaluations, etc.).

Output device 44 may include a wide variety of different output devices configured to provide different types of outputs to users. For example, output device 44 may include visual output devices (e.g., lights, etc.), audible output devices (e.g., beepers, buzzers, etc.) and/or tactile output devices (e.g., vibratory devices, etc.). Output devices 44 may be controlled by controller 34 and may be activated based on a variety of criteria, including inputs from force sensing member 26 (e.g., indicating excessive force measurements), vacuum sensor 36 (e.g., indicating an improper vacuum level or potential problems with socket assembly 12), power supply 42 (e.g., indicating a low power level for one or more batteries), etc. Other types of output devices may be used according to various other embodiments, and the output devices may be activated based on a number of additional inputs beyond those described herein. Further, any conventional output devices may be utilized, and the output devices may be positioned at any suitable location on device 10.

Transceiver 46 may be a wireless transceiver configured to establish wireless communications with a remote terminal 47 or other device. Transceiver 46 may be configured to communicate using a variety of communication protocols (e.g., Bluetooth communications, infrared communications, 802.11x (e.g., Wi-Fi) communications, cellular communications, etc.) and with a wide variety of remote terminals 47 (e.g., personal digital assistants (PDAs), laptop computers, desktop computers, server computers, etc.). Furthermore, in some embodiments, remote terminal 47 may be a terminal usable by a user of device 10 (e.g., such that a user may provide inputs to and/or receive outputs from control system 18 while the user is wearing device 10). For example, terminal 47 may be a wearable device configured to be wearable on a belt of a user, worn on the wrist of a user, etc. Alternatively, remote terminal 47 may be a computer used by a clinician or physician in a clinical setting to evaluate, calibrate, modify, etc. device 10.

It should be understood that device 10 may include additional components to those described herein that may be used in the operation of device 10. For example, one or more valves (e.g., a check valve, solenoid valve, etc.) may be provided in line with fluid connection 29 between vacuum pump 38 and socket assembly 12 such that air/fluid is permitted only to exit socket assembly 12 via fluid connection 29. Other components may be added according to various other embodiments as understood by those skilled in the art.

Figure 6:
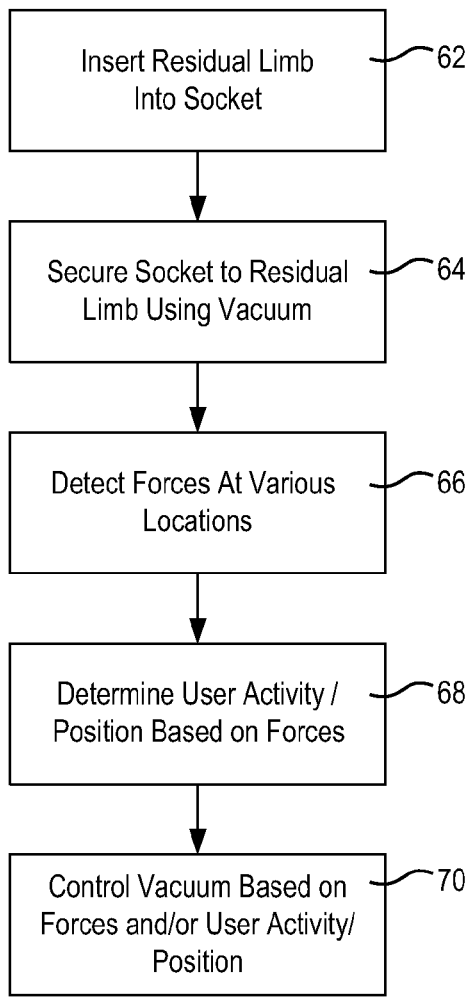
FIG. 6 is a flowchart illustrating a method of controlling a vacuum level of the prosthetic device of FIG. 1 according to an exemplary embodiment.

Referring now to FIG. 6, a block diagram of a method of controlling the vacuum level for device 10 is shown according to an exemplary embodiment. First, a residual limb is secured to a socket assembly (step 62). For example, as discussed in detail herein, a user may first apply an inner liner to a residual limb, and then insert the residual limb and inner liner into an outer casing. Next, the residual limb is secured to the socket assembly through application of a vacuum to the void created between the residual limb and the outer casing (step 64). According to various exemplary embodiments, the initial vacuum level maybe preset by the user and/or a clinician. According to other embodiments, the initial vacuum level may be determined by controller 34 based on any of a number of inputs from the various sensors disclosed herein. Next forces are detected at various locations about the residual limb by force sensing member 26 (step 66) and corresponding signals are provided from force sensing member 26 to controller 34. Controller 34 then determines a likely user activity (e.g., mode of ambulation, activity such as driving, sitting, standing, etc.) and/or an orientation of device 10 based on the signals received from force sensing member 26 (step 68). Based on the signals received from force sensing device 26 and/or the determined activity/orientation, controller 34 then controls vacuum pump 38 accordingly (step 70). For example, controlling pump 38 may include activating/deactivating pump 38, increasing/decreasing the rate of operation of pump 38, etc. Steps 66-70 may then be repeated on a continuous, intermittent, or other basis to maintain the vacuum level within socket assembly 12 at a proper level.

Figure 7:
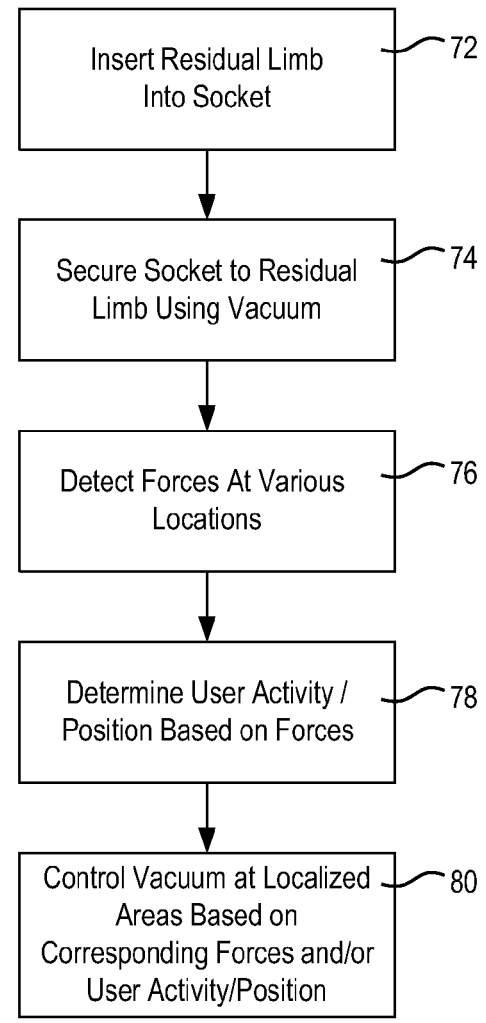
FIG. 7 is a flowchart illustrating a method of controlling a vacuum level of the prosthetic device of FIG. 1 according to an exemplary embodiment.

Referring now to FIG. 7, a block diagram of a method of controlling the vacuum level for device 10 is shown according to another exemplary embodiment. The method illustrated in FIG. 7 is in many aspects similar to the method illustrated in FIG. 6. However, according to an exemplary embodiment, the method illustrated in FIG. 7 provides the additional feature of detecting forces and controlling vacuum levels on a more localized basis (e.g., such that forces may be detected, and the vacuum controlled, for different localized regions of socket assembly 12).

First, a residual limb is secured to a socket assembly (step 72). Next, the residual limb is secured to the socket assembly through application of a vacuum to the void created between the residual limb and the outer casing (step 74). Next forces are detected at various locations about the residual limb by force sensing member 26 (step 76) and corresponding signals are provided from force sensing member 26 to controller 34. Controller 34 then determines a likely user activity (e.g., mode of ambulation, activity such as driving, sitting, standing, etc.) and/or an orientation of device 10 based on the signals received from force sensing member 26 (step 78). Based on the signals received from force sensing device 26 and/or the determined activity/orientation, controller 34 then controls vacuum pump 38 accordingly (step 80). As indicated above, the vacuum level within socket assembly 12 may be controlled on a localized basis based on the various forces detected by force sensing member 26. For example, a portion of the residual limb may be divided into a number of localized regions, and force sensor 26 may be configured to detect at least one force for each localized region. Controller 34 may then in turn control the vacuum level (e.g., control pump 38 so as to maintain, increase, or decrease a vacuum level in a particular localized region) in each localized region based on the forces being experienced by that specific region. For example, controlling pump 38 may include activating/deactivating pump 38, increasing/decreasing the rate of operation of pump 38, etc. Steps 76-80 may then be repeated on a continuous, intermittent, or other basis to maintain the vacuum level within socket assembly 12 at a proper level.

Figure 10:
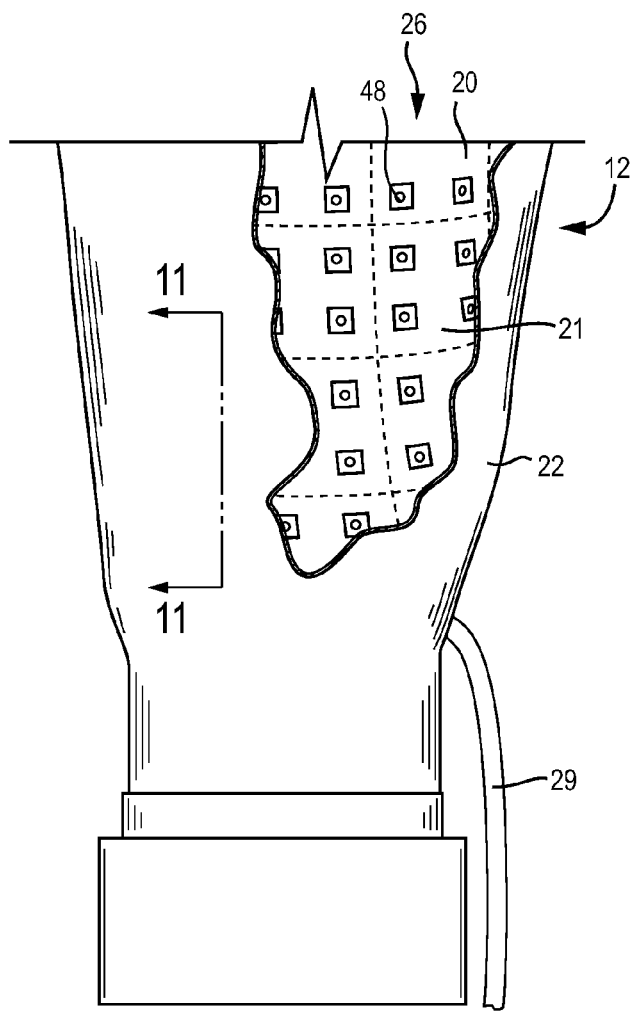
FIG. 10 is a partially cutaway perspective view of a socket assembly of the prosthetic device of FIG. 1 according to another exemplary embodiment.
Figure 11:
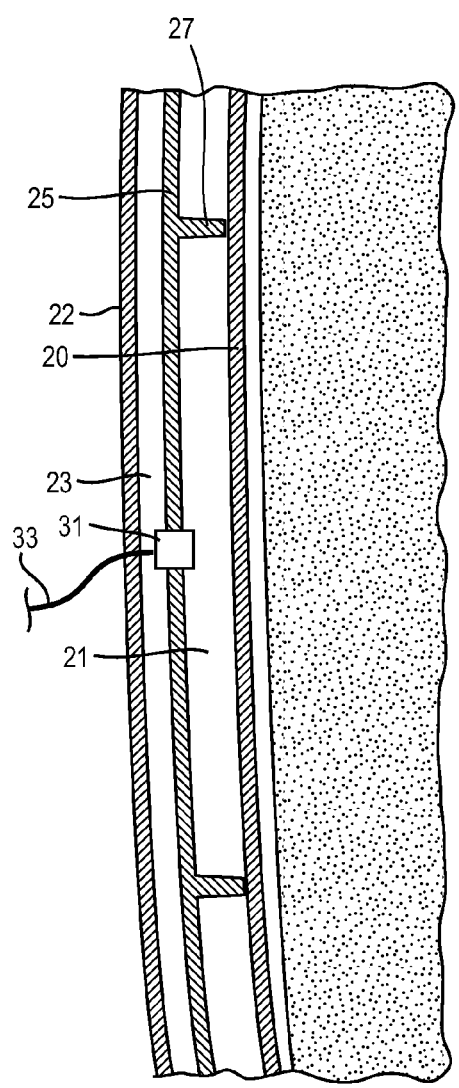
FIG. 11 is a partial cross section view of a portion of the socket assembly of FIG. 10 according to an exemplary embodiment.

An exemplary embodiment of a portion of a socket assembly that may provide for localized control of vacuum with the socket assembly is shown in FIGS. 10-11. As shown in FIGS. 10-11, in order to provide for localized control of vacuum, a manifold 25 may be provided within outer casing 22 and may define a number of regions 21, each region 21 being defined by a number of dividers 27. According to one embodiment, dividers 27 are provided on an inner surface of manifold 25 (e.g., by debossing the inner surface of manifold 25) such that dividers 27 form localized regions 21 that can each have different vacuum levels. As shown in FIG. 11, the localized regions 21 may in turn all be in fluid communication via an intermediate space 23. For example, in one embodiment, each region 21 may be in fluid communication with intermediate space 23 by way of a valve 31 (e.g., a check valve, etc.). Each valve 31 may control fluid communication between intermediate space 23 and each localized region 21, such that by controlling whether a particular valve 31 is open or closed, a vacuum applied to intermediate space 23 (e.g., via fluid connection 29) may in turn be selectively applied to the localized region 21. In this way, the vacuum applied across the surface of the residual limb may be varied in response to the forces acting upon the residual limb. As shown in FIG. 11, each valve 31 may be controlled via a control line 33, or alternatively, via another type of wired or wireless connection.

According to some embodiments, in order to ensure proper sealing for localized regions 21, inner liner 20 may be customized to conform to manifold 25. For example, inner liner may include raised portions (e.g., detents, etc.) that are configured to align with or otherwise provide a complimentary fit with corresponding structure (e.g., dividers 27) on manifold 25. In other embodiments, portions of inner liner 20 may be configured to fit within debossed portions of manifold 25. In this way, both a vacuum and mechanical "lock" is formed between the socket assembly (e.g., each localized region 21) and the residual limb.

According to an alternative embodiment, rather than manifold 25 being provided to the interior of outer casing 22, a manifold may be coupled, for example, to the outer surface of outer casing 22 such that each localized region 21 has a fluid connection to the manifold, and the manifold controls distribution of the vacuum from fluid connection 29 to each localized region 21. Other types and arrangements of manifolds may be used according to various alternative embodiments. For example, the manifold may be integrated with the vacuum pump such that fluid communications to each localized region are provided from the vacuum pump.

According to an exemplary embodiment, each localized region 21 is associated with a single force sensor 48. According to other embodiments, each localized region 21 may be associated with a plurality of force sensors 48. Further, the force sensor(s) provided within each localized region 21 may be distributed evenly within the localized region, or unevenly distributed at desired locations.

According to various embodiments, controller 34 may be configured such that the vacuum level within cavity 28 may be controlled independent from inputs received from vacuum sensor 36 (e.g., in connection with one or both of the methods illustrated in FIGS. 6-7). In other words, the actual vacuum level may be controlled based on the forces detected by force sensing member 26, rather than vacuum sensor 36. In alternative embodiments, controller 34 may control vacuum pump 38 based on inputs received from force sensing member 26 in combination with inputs received from vacuum sensor 36 and/or any other sensors 40. Furthermore, controller 34 may be configured to provide control signals to force sensing member 26 such that the force detection method may be adjusted to vary the frequency or pattern at which force sensors 48 detect forces/pressures applied to the residual limb. For example, based on a variety of factors (e.g., force measurements, a determined user orientation/activity/mode of ambulation, etc.) the rate at which force sensors detect forces may be adjusted accordingly. In one embodiment, controller 34 may be configured to provide a "sleep" mode such that the rate at which forces are detected and/or signals are sent to controller 34 is significantly reduced, which in turn conserves power for device 10. This type of control may be via signals provided directly to force sensors 48, or may be via signals sent to control electronics coupled to inner liner 20 that in turn control the operation of force sensors 48.

According to yet further embodiments, controller 34 may be configured to control the operation of pump 38 based on signals received over a period of time from one or more sensors (e.g., force sensors 48, vacuum sensor 36, other sensors 40, etc.). For example, based on changes in force over a period of time, controller 34 may determine a likely mode of ambulation (walking, jogging, running, etc.), whether a user is generally standing still or moving, whether a user is sitting, standing, etc., and the like. Various algorithms may be utilized in taking into account changes in force over time, and controller 34 may be configured to make other determinations than those described herein. According to various other embodiments, controller 34 may be configured to receive signals corresponding to specific movements of a user (e.g., a series of quick downward pressures, or a similar pattern that may not normally occur during normal use of device 10) and to trigger a specific mode (e.g., a predefined mode, a user/clinician defined mode, etc.) of operation for device 10 (e.g., a sleep mode, a low vacuum level mode, etc.). Controller 34 may be further configured to return to normal operation in response to yet other signal types (e.g., signals corresponding to a sudden increase in experienced forces due to a user standing up, etc.).

In some embodiments, shielding may be incorporated into the prosthetic device to protect the system components and minimize interference to the various signals being transmitted. For example, an shield member (e.g., an at least partially conductive member) may provide protection from electrostatic discharge (ESD) and minimize radio frequency interference (RFI), electromagnetic interference (EMI), and/or other interference that may be created by operation of the various force sensors and other components of the prosthetic device.

It should be understood that as used herein, the term "applying a vacuum" and similar terms generally refer to operating a vacuum pump in fluid communication with a cavity so as to generate a partial vacuum (e.g., a space of reduced gas pressure) within the cavity. The partial vacuum in turn creates a suction force that is applied to a residual limb and a socket assembly to maintain a proper fit between the components.

The prosthetic device shown in the various embodiments illustrated herein may provide benefits over more traditional prosthetic devices. For example, because vacuum levels may be controlled based on force measurements, the prosthetic device is able to automatically accommodate changes in atmospheric pressure by increasing/decreasing the amount of vacuum applied in response to changes in forces detected. As such, is some embodiments the use of a separate barometric pressure sensor may be unnecessary. Furthermore, the force sensors may be positioned in any desired location, and the locations may be customized to a particular user of a prosthetic device by a user and/or a clinician. Further yet, the prosthetic device may be configured such that after an initial configuration/calibration of the prosthetic device (e.g., the control system and associated components), the prosthetic device automatically maintains specific desired levels of socket pressure based on user activity or other factors, without the need for any input from users/clinicians or any additional user interfaces, etc. Additionally, the prosthetic device may be configured to detect "milking" or "pistoning" of the distal end of the residual limb (e.g., based on forces detected over a period of time) and automatically adjust the vacuum applied to the socket assembly to minimize these conditions.

It is important to note that the construction and arrangement of the elements of the prosthetic device as shown in the exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the embodiments. For example, for purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. A method of controlling an amount of vacuum to a cavity of a prosthetic limb, the method comprising:
    applying the amount of vacuum to the cavity defined by a socket of the prosthetic limb and a portion of a residual limb of a user, the portion of the residual limb received within the socket, wherein the cavity includes a plurality of localized regions defined by dividers embossed in a manifold of an outer casing of the prosthetic device, wherein the manifold includes a plurality of control valves, wherein each control valve of the plurality of control valves is associated with a different localized region;
    detecting forces experienced by the residual limb at a plurality of locations about the portion of the residual limb during use of the prosthetic device by the user using a plurality of force sensors, wherein the plurality of force sensors are distributed unevenly such that there are fewer force sensors positioned near lateral sides of the residual limb than positioned near an anterior side and a posterior side of the residual limb;

providing signals to a controller based on the forces detected at the plurality of locations; and controlling the amount of vacuum applied to the cavity based on the signals by selectively opening and closing the each of the control valves of the plurality of control valves such that vacuum applied across a surface of the residual limb is varied by localized region.

2. The method of claim 1, wherein the amount of vacuum applied to the cavity is controlled independent from a detected vacuum level within the cavity as detected by a vacuum sensor.

3. The method of claim 1, further comprising determining an activity of a user based at least in part on the signals and controlling the amount of vacuum based on the determined activity, wherein the activity comprises one of standing, sitting, and walking.

4. The method of claim 1, further comprising determining an orientation of the prosthetic device based on the signals.

5. The method of claim 1, further comprising determining a mode of ambulation based on the signals.

6. The method of claim 1, wherein the controller is configurable to control the amount of vacuum applied to the cavity based only on the signals.

7. A method comprising:

detecting forces experienced by a residual limb at a plurality of locations about a portion of the residual limb during use of a prosthetic device using a plurality of force sensors, each force sensor located adjacent one of the plurality of locations, wherein the plurality of force sensors are arranged in a matrix;

providing signals to a controller based on the forces detected at the plurality of locations; and selectively controlling an amount of vacuum applied to each of a plurality of localized regions on the residual limb based on the signal, wherein each of the localized regions is defined by dividers embossed in a manifold of an outer casing of the prosthetic device, wherein the manifold includes a plurality of control valves, wherein each control valve of the plurality of control valves is associated with a different localized region, wherein selectively controlling the amount of vacuum applied to each of the plurality of localized regions includes selectively opening and closing the each of the control valves of the plurality of control valves such that vacuum applied across a surface of the residual limb may be varied by localized region.

8. The method of claim 7, further comprising:

selectively controlling the amount of vacuum applied to each of the plurality of localized regions independent from a measured vacuum level within each localized region.

9. The method of claim 7, wherein the prosthetic device comprises a socket assembly having a manifold configured to selectively control the amount of vacuum provided from a vacuum pump to each localized region.

10. The method of claim 7, wherein each localized region is associated with at least one force sensor.

* * * * *